US00PP08642P

United States Patent [19]

Van der Jagt

[11] Patent Number: Plant 8,642

[45] Date of Patent: Mar. 15, 1994

[54] CHRYSANTHEMUM NAMED REAGAN

[75] Inventor: Martinus Van der Jagt, CJ Langeraar, Netherlands

[73] Assignee: Chrysanthemum Breeders Association, N.V., Netherlands Antilles

[21] Appl. No.: 780,305

[22] Filed: Oct. 22, 1991

[51] Int. Cl.[5] ..... A01H 5/00

[52] U.S. Cl. ..... Plt./82.4

[58] Field of Search ..... Plt. 74.1, 82.4

*Primary Examiner*—Howard J. Locker

*Attorney, Agent, or Firm*—Parkhurst, Wendel & Rossi

[57] ABSTRACT

A new and distinct cultivar of Chrysanthemum plant named Reagan, bearing medium sized pale pink blooms with a yellow-green center and a performance of 24–28 days.

2 Drawing Sheets

The present application is related to the following co-pending applications:

| Application No. | Filing Date | Title |
|---|---|---|
| 07/780,304 | October 22, 1991 | Salmon Reagan |
| 07/780,237 | October 22, 1991 | Orange Reagan |
| 07/780,332 | October 22, 1991 | Dark Reagan |
| 07/780,292 | October 22, 1991 | Coral Reagan |
| 07/767,791 | September 30, 1991 | Sulfur Reagan |
| 07/767,881 | September 30, 1991 | Yellow Reagan |
| 07/780,238 | October 22, 1991 | Bronze Reagan |
| 07/780,233 | October 22, 1991 | White Reagan" |

ORIGIN AND HISTORY OF THE NEW PLANT

The new plant of the present invention comprises a new and distinct cultivar of Chrysanthemum plant which is a cross of unknown *Chrysanthemum morifolium* parents. The new and distinct cultivar was a seedling resulting from the open pollination among groups of chrysanthemum cultivars maintained under the control of the inventor for breeding purposes. The new and distinct cultivar was discovered in a greenhouse in Ter Aar, Holland in 1986. The invention has been asexually reproduced by cuttings in greenhouses at Ter Aar, Holland. The new cultivar has been found to retain its distinctive characteristics through successive propagations.

SUMMARY OF THE NEW PLANT

The present invention is a new and distinct variety of Chrysanthemum of a medium sized bloom and pink color.

BRIEF DESCRIPTION OF THE DRAWINGS

The present new and distinct chrysanthemum cultivar is shown in the accompanying drawings, the color being as nearly true as possible with color photographs of this type.

Sheet 1 shows the full bloom of the new cultivar;

Sheet 2, top, shows various stages of bloom of the new cultivar; and

Sheet 2, bottom, shows the foliage and petiole of the new cultivar.

DESCRIPTION OF THE INVENTION

This new variety of chrysanthemum is of the botanical classification *Chrysanthemum morifolium*, and is named Reagan. When grown in the vicinity of Ter Aar, Holland, it has a response time of approximately 7½ weeks. This new variety produces medium sized pink blooms with a yellow green center having a 4 week performance (i.e., a vase life of 24–28 days). This new variety of chrysanthemum has been found to retain its distinctive characteristics throughout successive propagations and may be planted under greenhouse conditions in Holland between weeks fifty and thirty-five (i.e., between December 1 and August 30). Pest resistance, disease resistance and frost tolerance are unknown.

The following is a description of the plant and characteristics (color designations are from RHS Color Chart) that distinguish it over related known varieties and its antecedents:

Botanical classification: *Chrysanthemum morifolium.*

Bud:

*Size.*—Medium (cross section±1.0 cm, height±0.7 cm.

*Form.*—Round and flat.

*Outside color.*—Grape-purple 186D but paler.

Bloom:

*Size.*—Medium.

*Fully expanded.*—6½–7 cm.

*Borne.*—Upper portion, single flower per peduncle; lower portion, plural flowers per peduncle.

*Stems.*—Strong, thick.

*Forms.*—Single (daisy).

*Performance.*—Very good 24–28 days (18°–20° C.).

Color:

*Center of flower.*—Immature: yellow green 151 C. Mature: yellow green 154 A.

*Base of petals.*—Purple 75 B.

*Inside of petals.*—Purple 75 B.

*Reverse of petals.*—Red purple 69 A but paler.

*Outer petals.*—Red purple 75 B.

*Tonality from a distance.*—A pale pink daisy with a fresh looking center having little or no pollen.

*Discoloration.*—Some to red purple 69 D.

*Pollen.*—Yellow-orange 14A.

Petals:

*Texture.*—Upperside smooth, underside smooth.

*Number.*—24–30 (two rows).

*Cross-section.*—Flat, two keels.

*Arrangements.*—Imbricated.

*Persistance.*—Good. Petals keep straight or reflex somewhat at the edge at the end of blooming.

*Fragrance.*—Typical Chrysanthemum.

*Disc diameter.*—1.5 cm.

Reproductive organs:

*Stamen.*—Yellow, thick, 3 mm in length.

*Pollen.*—Appears at a late stage of blooming yellow orange in color.

*Styles.*—Green thick.

*Length.*—±5 mm.

*Stigmas.*—Yellow.

*Width.*—±1 mm.

*Ovaries.*—Enclosed in calyx.

Plant:

*Form.*—Spray mum meant for erect culture. Herbaceous.

*Growth.*—Strong.

*Height.*—100–125 cm.

*Peduncle.*—Near the top ±14 cm, near the middle ±24 cm, near the bottom ±28 cm.

*Internodes.*—3 cm.

*Flowering response.*—7½ weeks.

Foliage:

*Color.*—Upperside green 137 A. Underside 137 C.

*Size.*—Length ±12 cm. Width ±9 cm.

*Quantity.*—22–28.

Shape.—Lobed, see photograph.

*Texture.*—Upperside rough. Underside smooth, slightly hirsute.

*Ribs and veins.*—Ribs well developed. Veins not so developed.

*Edge.*—Crenated.

Distinguishing characteristics of the chrysanthemum of the Reagan family are summarized below in the Table. Each of the titled Reagans having a color designation is an induced mutation by irradiation of Reagan.

TABLE IA

| U.S. Application Ser. No. Title | 07/780,305 Reagan | 07/780,223 White Reagan | 07/780,292 Coral Reagan |
|---|---|---|---|
| bud outside color | greyed-purple 186d but paler | yellow 4d | greyed-purple 186a |
| center of flower | | | |
| immature: | yellow-green 151c | yellow-green 151c | yellow-green 151c |
| mature: | yellow-green 154a | yellow-green 154a | yellow-green 154a |
| base of petals | purple 75b | white 155d but whiter and brighter | greyed-red 179c but redder |
| inside of petals | purple 75b | white 155d but whiter and brighter | greyed-red 179c but redder |
| reverse of petals | red-purple 69a but paler | white 155d but whiter and brighter | greyed-yellow 162d tinged with red-purple 71b between ribs and margin |
| outer petals | purple 75b | white 155d but whiter and brighter | greyed-red 179c but redder |
| petal cross-section | flat | flat | flat |

TABLE IA-continued

| U.S. Application Ser. No. Title | 07/780,332 Dark Reagan | 07/780,237 Orange Reagan | 07/780,238 Bronze Reagan |
|---|---|---|---|
| bud outside color | between greyed purple 186a and b | greyed-red 180a | greyed-red 179c |
| center of flower | | | |
| immature: | yellow-green 151c | yellow-green 151c | yellow-green 151c |
| mature: | yellow-green 154a | yellow-green 154a | yellow-green 154a |
| base of petals | red-purple 69b lightly overlaid with red-purple 72a giving an overall impression of purple 75a but pinker | between greyed orange 169a and b | yellow 8a with an overlay of greyed red 179b |
| inside of petals | red-purple 69b lightly overlaid with red-purple 72a giving an overall impression of purple 75a but pinker | between greyed orange 169a and b | yellow 8a with an overlay of greyed red 179b |
| reverse of petals | red-purple 69c with a light tessellation of red-purple 72a | nearest to greyed-orange 163b tinged with red between the ribs | yellow 8c tinged along the center with greyed red 179b in a tesselated pattern |
| outer petals | red-purple 69b lightly overlaid with red-purple 72a giving an overall impression of purple 75a but pinker | between greyed-orange 169a and b | yellow 8a with an overlay of greyed red 179b |
| petal cross-section | convex | convex | flat |

| U.S. Application Ser. No. Title | 07/767,881 Yellow Reagan | 07/767,791 Sulphur Reagan | 07/780,304 Salmon Reagan |
|---|---|---|---|
| bud outside color | yellow 9c | yellow 10c | Nearest to yellow-orange 23d |
| center of flower | | | |
| immature: | yellow-green 151c | yellow-green 151c | yellow-green 151c |
| mature: | yellow-green 154a | yellow-green 154a | yellow-green 154a |
| base of petals | yellow 5c | yellow 6d | nearest to orange 29c |
| inside of petals | yellow 5c | yellow 6d | nearest to orange 29c |
| reverse of petals | yellow 4c | yellow 6d | nearest to yellow-orange 22d |
| outer petals | yellow 5c | yellow 6d | nearest to orange 29c |
| petal cross-section | flat | flat | flat |

What is claimed is:

1. A new and distinct cultivar of Chrysanthemum, named Reagan, as described and illustrated.

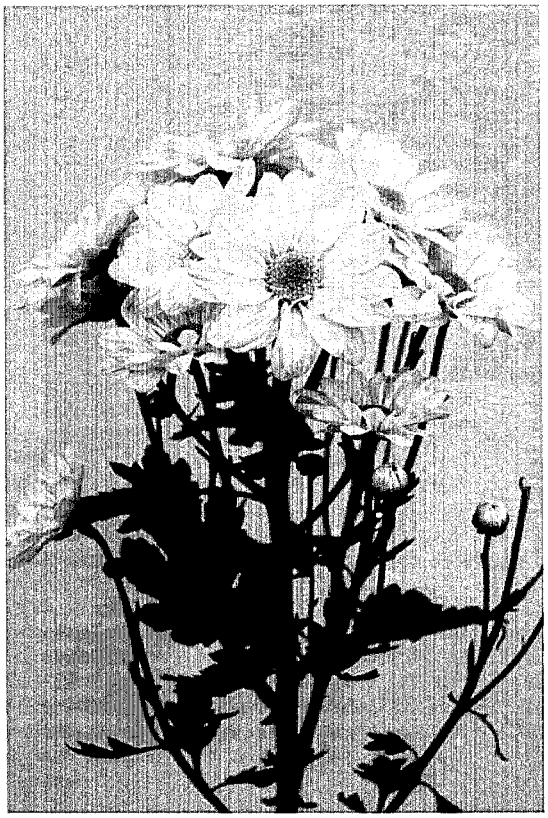

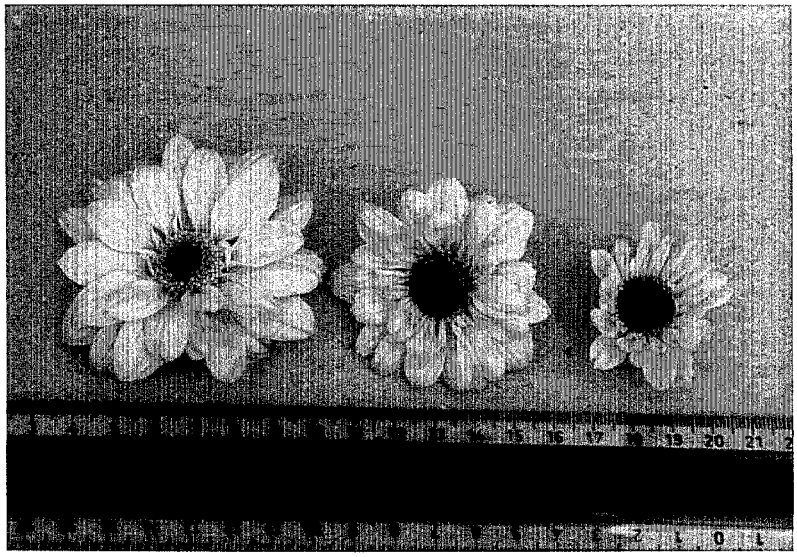
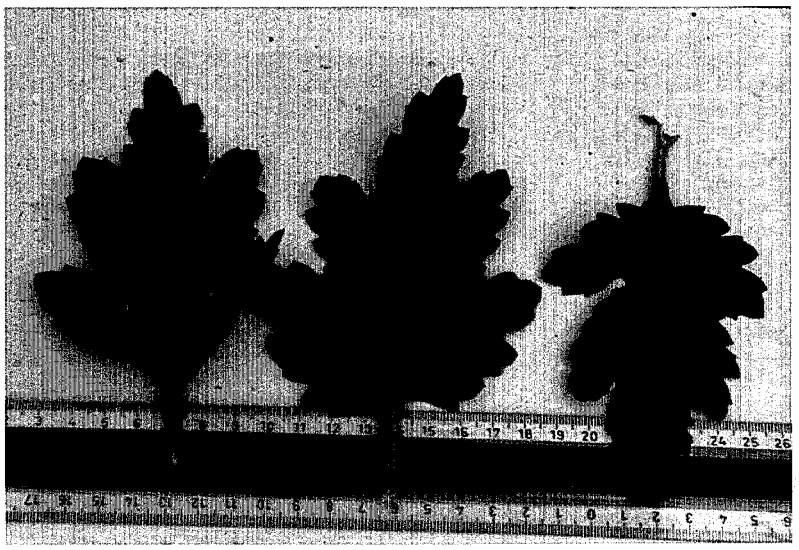

* * * * *